Figure 1:
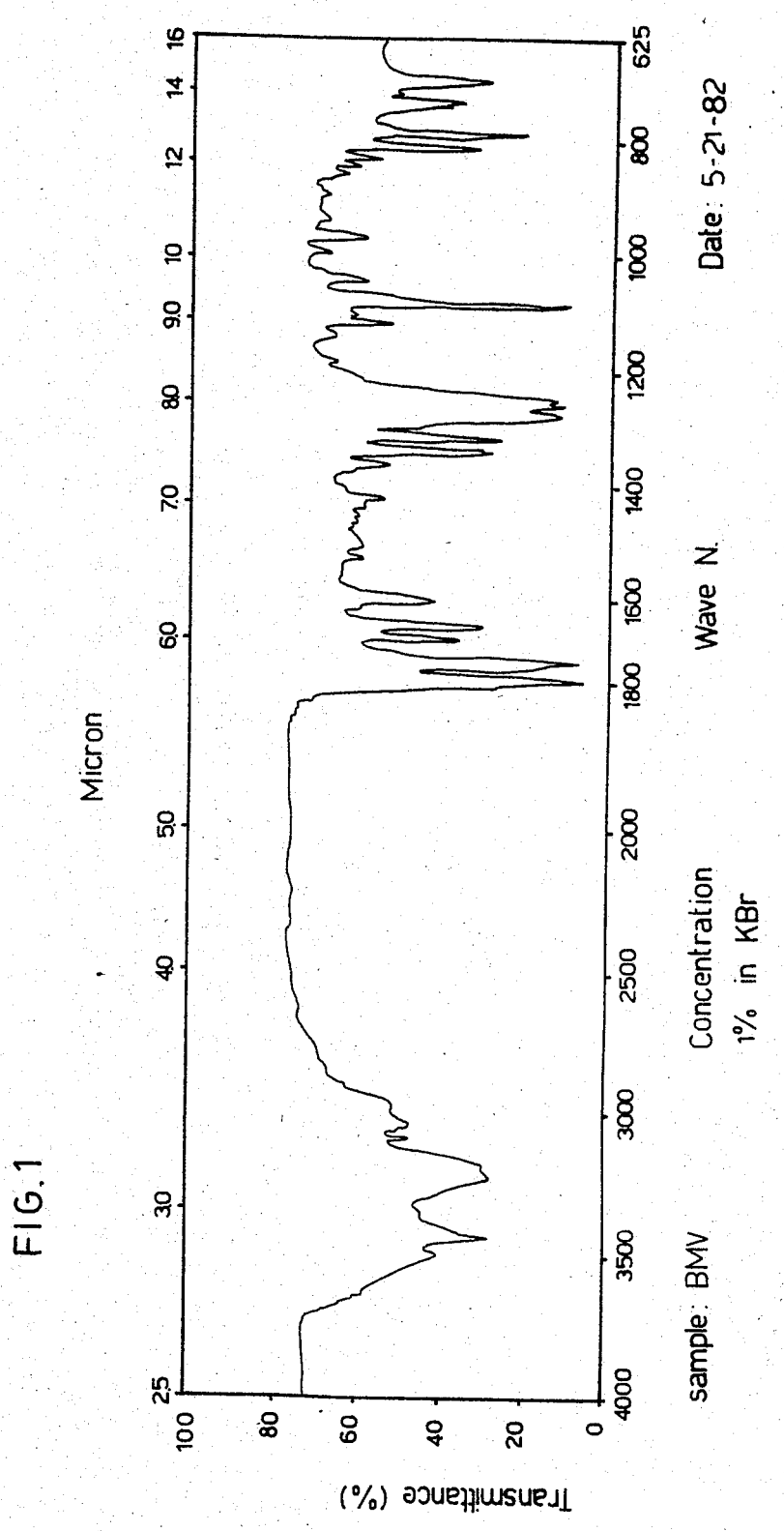

United States Patent [19]

Ghelli et al.

[11] Patent Number: 4,568,745

[45] Date of Patent: Feb. 4, 1986

[54] ADDUCT OF MUTUALLY STABILIZING MENADIONE AND THIAMINE

[75] Inventors: Giovanni Ghelli, Savona; Alessandro Barbon, Arluno; Luciano Conti, Palassolo Milanese; Luigi Oliari, Pavia, all of Italy

[73] Assignee: Luigi Stoppani S.p.A., Milan, Italy

[21] Appl. No.: 506,847

[22] Filed: Jun. 22, 1983

[30] Foreign Application Priority Data

Jun. 24, 1982 [IT] Italy ............................. 22051 A/82

[51] Int. Cl.$^4$ .................... C07D 239/02; A61K 31/51
[52] U.S. Cl. .................................... 544/327; 514/252
[58] Field of Search ............... 544/327; 424/255, 331; 514/252

[56] References Cited

U.S. PATENT DOCUMENTS

| | | | |
|---|---|---|---|
| 3,931,152 | 1/1976 | Tomcufcik et al. | 260/239 BC |
| 4,006,234 | 2/1977 | Child et al. | 424/251 |
| 4,102,806 | 7/1978 | Kondo et al. | 252/316 |
| 4,275,154 | 6/1981 | Hall | 435/32 |

OTHER PUBLICATIONS

Eligio Perucca, "Dizionario D'Ingegneria", (Dictionary of Engineering)—Annex A$_1$—vol. VI—p. 706.
Eligio Perucca, "Dizionario D'Ingegneria", (Dictionary of Engineering)—Annex A$_2$—vol. VII—p. 489.
Eligio Perucca, "Dizionario D'Ingegneria", (Dictionary of Engineering)—Annex A$_3$—vol. VII—p. 490.

*Primary Examiner*—Donald G. Daus
*Assistant Examiner*—Cecilia Shen
*Attorney, Agent, or Firm*—Fleit, Jacobson, Cohn & Price

[57] ABSTRACT

An adduct of menadione and thiamine is described having the general formula $C_{34}H_{36}N_4O_{11}S_3$, molecular weight 772.84 and containing the components in a molecular ratio of 2:1 respectively.

This adduct is particularly intended to be added to integrator mixtures for zootechny.

3 Claims, 5 Drawing Figures

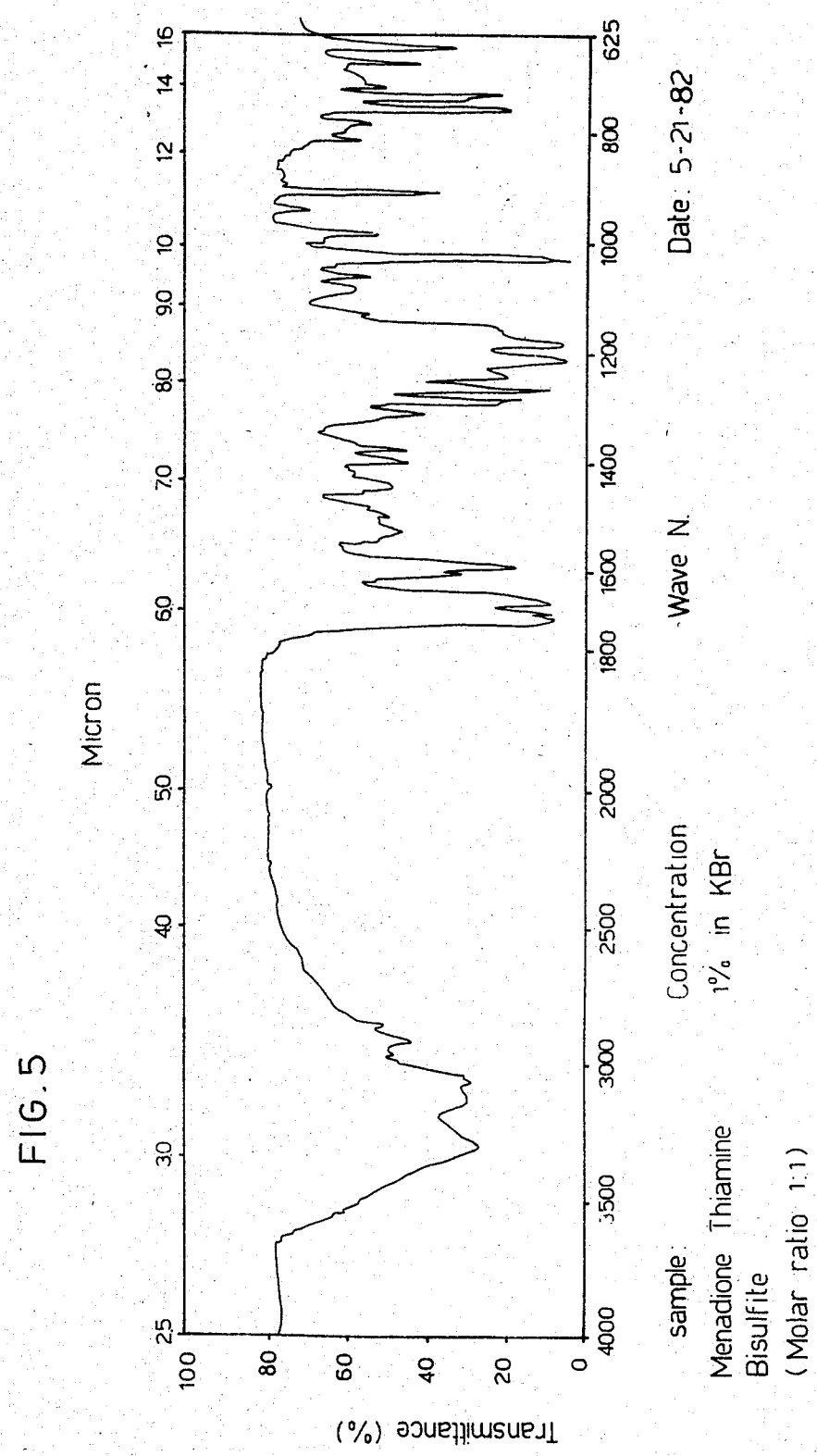

ADDUCT OF MUTUALLY STABILIZING MENADIONE AND THIAMINE

The inventor of the present invention had already described, in a preceding application (Italy No. 26008 A/78), new adducts of compounds having K-vitaminic (menadione sodium bisulfite) activity, which were stabilized by compounds also endowed with therapeutical, particularly vitaminic, activity.

Said adducts represented a remarkable improvement in comparison with other previously used K-vitaminic adducts, wherein the stabilizing portion of the adduct was inert from the therapeutical point of view.

One of the stabilized adducts, particularly claimed in the above mentioned Italian application, was the stabilized menadione sodium bisulfite and thiamine hydrochloride adduct, said components being presented in a molecular ratio of 1:1 respectively.

This menadione sodium bisulfite-thiamine adduct has the general formula $C_{33}H_{27}ClN_4O_6S_2$, a molecular weight of 555.17 and therefore a theoretical content of menadione ($C_{11}H_8O_2$) and thiamine, this latter expressed as thiamine hydrochloride (i.e. $C_{12}H_{18}Cl_2N_4OS$), of 31.0% b.w. and 60.8 b.w. respectively. This means that the above adduct derives from a mole to mole reaction between menadione sodium bisulfite and thiamine hydrochloride, with elimination of one molecule of sodium hydrochloride.

As aforesaid, the stabilization of said adduct, particularly by means of another compound, also having a therapeutical activity, was claimed in the above mentioned application.

Further initimate experimental studies about said adducts surprisingly led to identify another compound, which was also obtained by reacting menadione sodium bisulfite with thiamine hydrochloride, but in a ratio of 2:1 respectively; namely the elimination of two sodium hydrochloride molecules and the addition of menadione bisulfite with thiaminic rest takes place; so that this new adduct has the formula $C_{34}H_{36}N_4O_{11}S_3$, molecular weight 772.84 and menadione and thiamine hydrochloride equivalent contents of 44.56% b.w. and 43.64% b.w. respectively; therefore it clearly differs from the above adduct in the composition. It differs also from the above adduct in another decisive characteristic; namely a mutual stabilization sets up between the adduct portions, so that the K-vitamin stabilizes the thiamine and at the same time the thiamine stabilizes the K-vitamin.

Thanks to said characteristics, the product according to this invention represents a clear progress in comparison with the product of the preceding application, particularly as regards its use in the field of feed preparation, namely of the "integrators to the animal feeding".

Indeed both active principles, expressed as menadione and thiamine hydrochloride, the presence of which is essential in feed integrators, are generally added to these latter in the same amounts, by weight, and separately, so being dispersed into a medium, which is particularly apt to aid the loss of their respective activities.

On the contrary the use of the new product, subject of the present application, represents an important improvement (in this particular field) in that it allows on the one hand the contemporaneous introduction—namely in one only and precisely dosed addition—of both components, in the integrator; on the other hand the introduction of an adduct in the integrator, the components of which are preliminary stabilized. In this way the integrator preparation is simplified and improved and, at the same time, the loss in course of time of the relative activities is reduced.

Actually an intramolecular stabilization (IMS) is carried out, namely, a chemical IMS, which, as supposable, makes the biological activity speedy and more active; as an alternative to the extra molecular stabilization (EMS), which is obtained by a physical covering operation of the product granules by a suitable protective membrane.

Consequently not only a technical, but also an economical advantage in the fed preparation is attained in this way.

To recapitulate, the adduct of this invention, having the general formula $C_{34}N_{36}N_4O_{11}S_3$, theoretically contains 44.56% of menadione and 43.64% of thiamine (expressed as thiamine hydrochloride) and is better described by its structure formula, reported in the enclosed figure, from which it results that this adduct is a 3-[(4 amino-2-methyl-5-pyrimidinyl-methyl)]-5-(2-hydroxyethyl-4-methylthiazole-bis(1-naphthoquinone-2-methyl-bisulfite)

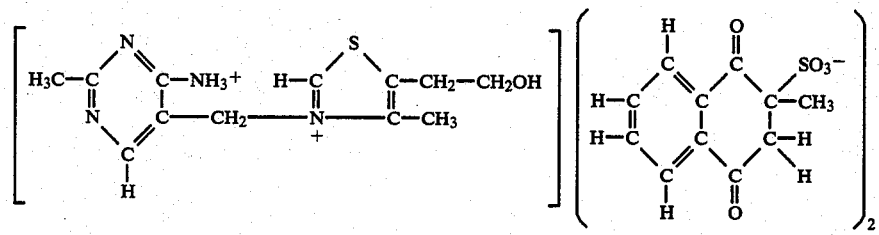

For convenience, however, the adduct according to the present invention will be hereinafter called BMV.

The adduct BMV is prepared according to the process which is illustrated in the following examples, which should not be considered as limiting this invention.

EXAMPLE 1

Laboratory preparation of the product in a pure form

A solution, consisting of 100 g of menadione sodium bisulfite (menadione-title 51.5%) and 200 g of water, is added with a solution consisting of 50 g of commercial thiamine hydrochloride (title 97%) and 50 g water, within about 10 minutes of agitation, at a temperature not higher than 30° C. After about 10 minutes since the addition of the thiamine solution was completed, the reaction product starts precipitating and, after 30–40 minutes of curing, under stirring, the product is filtered and washed until all hydrochlorides are off the filtrate; a white solid is so obtained, which is then vacuum dried at 40° C. up to a constant weight and the analized.

The chemical analysis gives:

| | |
|---|---|
| menadione (2 methyl 1-4 naphto-quinone) | 44.54% |
| thiamine (expressed as hydrochloride) | 43.63% |
| sodium hydrochloride | trace |
| water | absent |

Figure 2:
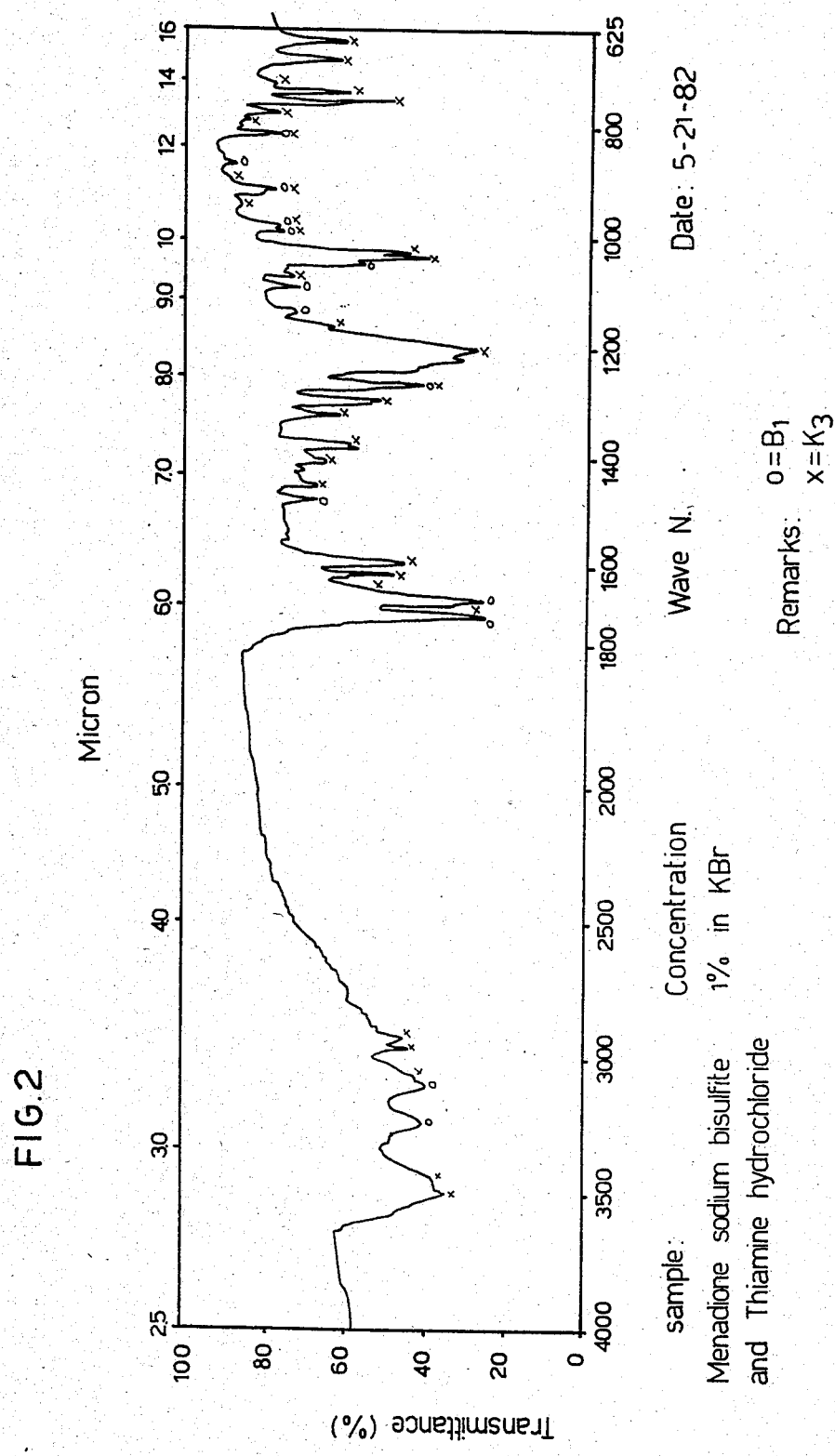

The so obtained product melts (with decomposition) at 188°-190° C. It shows a characteristic I.R. spectrum, as from FIG. 1 and from the comparison of the same with the spectra of FIGS. 2–5, which represent:

FIG. 2 the I.R. spectrum of simple physical mixture of menadione sodium bisulphite and thiamine hyudrochloride.

Figure 3:
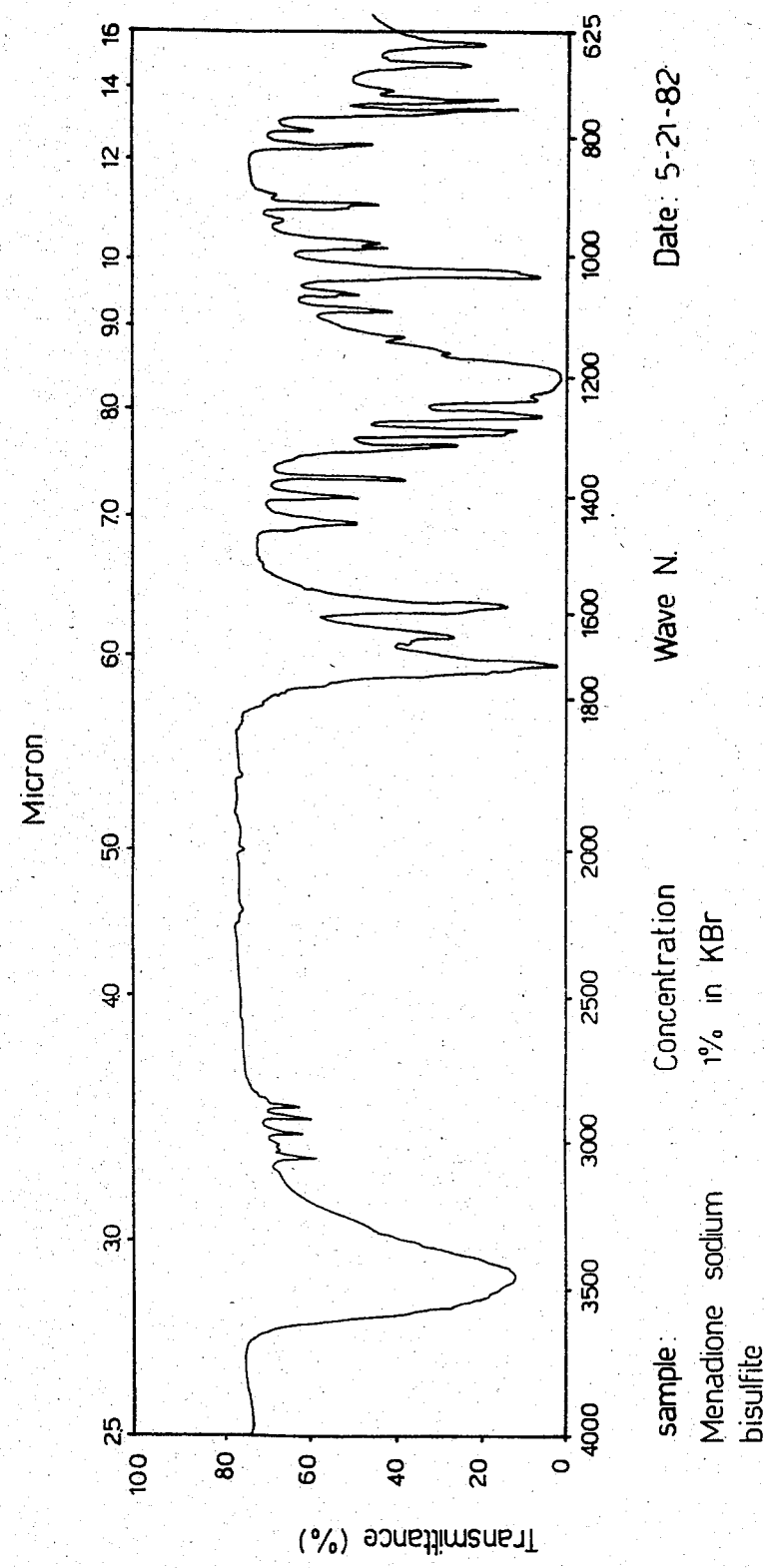

FIG. 3 the I.R. spectrum of menadione sodium bisulfite.

Figure 4:
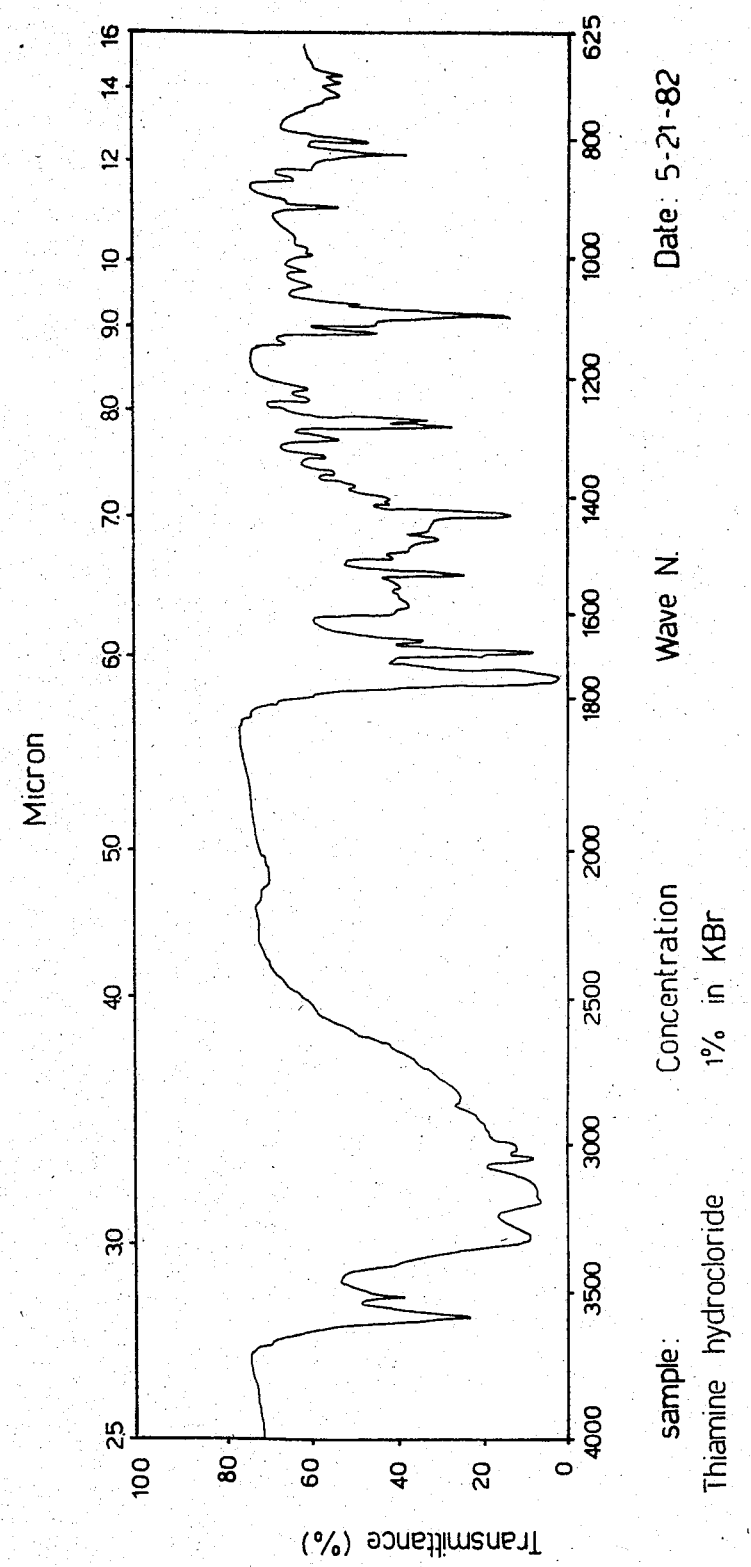

FIG. 4 the I.R. spectrum of thiamine hydrochloride.

FIG. 5 the I.R. spectrum of the mole to mole menadione bisulfite-thiamine adduct.

From the comparison of the above spectra it evidently appears that the BMW spectrum has a strong absorption band at 1740 cm$^{-1}$. This band does not appear in any other spectrum particularly neither in the adduct 2-1 spectrum nor in the physical mixture spectrum of the two active components.

The spectrum of physical mixture (FIG. 2) corresponds, by good approximation, to the summation of the spectra of the single components.

The elementary analysis gives the following results:
C=52.87% (the theoretical value for the adduct BMW=52.84%)
H=4.72% (the theoretical value for the adduct BMW=4.70%)
N=7.25% (the theoretical value for the adduct BMW=7.25%)
O=22.75% (the theoretical value for the adduct BMW=22.77%)
S=12.41% (the theoretical value for the adduct BMW=12.44%)

Therefore the obtained product perfectly corresponds (the 100%) to the formula $C_{34}H_{36}N_4O_{11}S_3$, which is the desired product. This product is water—as well as chloroform and ethyl alcohol—fairly soluble at a room temperature, namely:

in 100 g of water, dissolve 6 g of this product
in 100 g of chloroform dissolve 0.2 g of this product
in 100 g of ethyl alcohol dissolve 0.2 g of this product
The pH of saturated aqueous solutions is 3.3 at 25° C.

EXAMPLE 2

Experimental preparation on semi-industrial scale

To a solution of 100 g of commercial menadione sodium bisulfite (menadione title 49.5%) and 200 g water, 50 g of commercial thiamine hydrochloride (title 97%) are added, within five minutes under stirring, at a temperature not higher than 30° C. After 5 minutes, since the thiamine addition has been completed, the product starts precipitating. The stirring is protracted during 30 minutes and then the slurry is cooled to 0° C., filtered without washing and, after vacuum drying to 40° C., 100 g of white solid are obtained, this latter having the following analysis:

| | |
|---|---|
| menadione = | 43.66% |
| thiamine (as hydrochloride) = | 42.77% |
| NaCl = | 2.0% |
| H$_2$O = | 0 |
| or: the adduct BMV = | 98.0% |

-continued

| | |
|---|---|
| NaCl = | 2.0% |
| | 100.0% |

The yield is 88.2%.

EXAMPLE 3

Pilot preparation

This example represents a model for an industrial preparation of an adduct (BMV) according to the present invention.

A solution of 2 kg of commercial menadione sodium bisulfite (menadione title 51.29%) in 4 kg of a liquid, consisting of 2 kg of water and 2 kg of a filtrate recycled from a preceding preparation, is prepared.

To this solution, 1 kg of commercial thiamine hydrochloride (97%), within 10 minutes, at a temperature not higher than 30° C., is added; the thiamine hydrochloride dissolves and, after about 10 minutes, the product BMW starts precipitating. After 30 minutes of curing, the product is cooled to 0° C. and centrifugated without washing. After vacuum drying at 40° C., 2.25 kg of product having the following analysis are obtained:
BMW=96.6% (menadione 43%; thiamine hydrochloride equivalent=42%)
NaCl=3.4%
H$_2$O=0%
A product is so obtained which is pure up to 96.6%.

EXAMPLE 4

Stabilization tests of the product of this invention in feeds

In order to determine the stability of the product according to this invention, several mixtures of the adduct to be tested with aluminum silicate, having 10.4% moisture, (as a support) were prepared.

The tested mixtures were the following:
(A)=1,5 g product BMV+50 g aluminum silicate
(B)=1,5 g menadione sodium bisulfite+50 g aluminum silicate
(C)=0,75 g thiamine hydrochloride+50 g aluminum silicate The mixtures were placed in sealed containers and maintained at 55° C. in a thermostat for 3 different periods of times. It was observed:

after 1 day (24 hours): in the sample were still present:
(A)
  95.3% of the initially present menadione
  63.7% of the initially present thiamine hydrochloride
(B) 70.2% of the initially present menadione
(C) 47.2% of the initially present thiamine hydrochloride after 3 days (72 hours): in the sample where still present:
(A)
  92.0% of the initially present menadione
  28.7% of the initially present thiamine hydrochloride
(B) 23.1% of the initially present menadione
(C) 16.5% of the initially present thiamine hydrochloride

EXAMPLE 5

Comparison tests of the BMW product stability, present in integrator mixtures for zootechny as compared with menadione sodium bisulfite MSB and a thiamine hydrochloride in the same conditions The tests were carried out on three integrator types having the same percentage composition, which corresponds to a standard industrial use, namely:

| | |
|---|---|
| oligoelement mixture | 10.0% |
| vitamin mixture (vitamins different from K and B vitamin) | 3.5 |
| coline HCl 50% | 20.0% |
| support q.sb. | to 100 |

The support differs as following

| | |
|---|---|
| (A) Grape peels (with moisture) | 6.80% |
| (B) Maize gluten flour (with moisture) | 8.40% |
| (C) Grape peels + CaCO₃ (2:1)(with moisture) | 5.40% |

|  | % of the initially present menadione still present in the sample after the reported days | | | | | | | | % of initially present thiamine hydrochloride still present in the sample after the reported days | | | | | | | |
|---|---|---|---|---|---|---|---|---|---|---|---|---|---|---|---|---|
|  | At ambient temp. | | | | At 37° C. | | | | At ambient temp. | | | | At 37° C. | | | |
| Sample | 30 | 60 | 90 | 150 | 30 | 60 | 90 | 150 | 30 | 60 | 90 | 150 | 30 | 60 | 90 | 150 |
| A + MSB | 66 | 44 | 41 | 36 | 24 | 13 | 11 | 8 | / | / | / | / | / | / | / | / |
| B + MSB | 69 | 44 | 40 | 26 | 24 | 13 | 11 | 9 | / | / | / | / | / | / | / | / |
| C + MSB | 67 | 55 | 53 | 47 | 54 | 38 | 34 | 16 | / | / | / | / | / | / | / | / |
| A + adduct BMV | 75 | 74 | 68 | 63 | 74 | 72 | 59 | 49 | 90 | 91 | 83 | 67 | 94 | 90 | 86 | 59 |
| B + adduct BMV | 79 | 73 | 69 | 58 | 68 | 57 | 65 | 37 | 85 | 82 | 77 | 62 | 74 | 67 | 62 | 60 |
| C + adduct BMV | 74 | 71 | 86 | 75 | 75 | 67 | 68 | 53 | 88 | 84 | 80 | 73 | 88 | 84 | 78 | 59 |
| A + B₁HCl | / | / | / | / | / | / | / | / | 62 | 57 | 42 | 30 | 60 | 47 | 24 | 22 |
| B + B₁HCl | / | / | / | / | / | / | / | / | 71 | 55 | 44 | 42 | 55 | 48 | 46 | 35 |
| C + B₁HCl | / | / | / | / | / | / | / | / | 50 | 44 | 40 | 40 | 45 | 35 | 32 | 30 |

Practically an integrator generally contains the herein claimed adduct BMV in a ratio of 2.5 g to kg integrator.

What we claim is:

1. A menadione-thiamine adduct compound wherein the menadione (vitamin K₃) and thiamine (vitamin B₁) are reciprocally chemically linked in a ratio of 2:1 and stabilized through a mutual intramolecular (IMS) link by means of a reaction between menadione bisulfite and thiamine hydrochloride, 2 sodium chloride molecules being removed during said reaction, so that said menadione and thiamine are chemically stabilized, said stabilized menadione-thiamine adduct compound having the empirical formula $C_{34}H_3N_4O_{11}S_3$, and a molecular weight of 772.84, and wherein said chemically IMS stabilized compound keeps the individual vitaminic activities of both vitamin components intact.

2. A menadione-thiamine adduct compound according to claim 1, wherein said IMS stabilized 2 menadione-1 thiamine compound has the following specification: 3-[(4-amino-2-methyl-5-pyrimidinyl-methyl)]-5-(2-hydroxyethyl-4-methylthiazole-bis(1-4-naphthoquinone-2-methyl-bisulfite).

3. A menadione and thiamine adduct compound according to claim 1, which displays a vitaminic activity equivalent to 85.48% b.w. of $K_3.H_2O$ vitamin (corresponding to 44.56% b.w. of menadione) and 43.64% b.w. of vitamin $B_1$, respectively.

* * * * *